(12) United States Patent
Park et al.

(10) Patent No.: US 12,735,664 B2
(45) Date of Patent: Sep. 15, 2026

(54) CELL CULTURE DEVICE

(71) Applicant: AMOGREENTECH CO., LTD., Gimpo-si (KR)

(72) Inventors: Hee Sung Park, Gimpo-si (KR); In Yong Seo, Gimpo-si (KR); Seoung Hoon Lee, Gimpo-si (KR); Kyung Gu Han, Gimpo-si (KR); Seon Ho Jang, Gimpo-si (KR); Jae Yun Kim, Gimpo-si (KR); Su Yeon Lee, Gimpo-si (KR); Ji Young Kim, Gimpo-si (KR); Hyo Jung Lee, Gimpo-si (KR)

(73) Assignee: AMOGREENTECH CO., LTD., Gimpo-si (KR)

( * ) Notice: Subject to any disclaimer, the term of this patent is extended or adjusted under 35 U.S.C. 154(b) by 1041 days.

(21) Appl. No.: 17/754,994

(22) PCT Filed: Oct. 12, 2020

(86) PCT No.: PCT/KR2020/013852
§ 371 (c)(1),
(2) Date: Apr. 18, 2022

(87) PCT Pub. No.: WO2021/075806
PCT Pub. Date: Apr. 22, 2021

(65) Prior Publication Data

US 2022/0389360 A1 Dec. 8, 2022

(30) Foreign Application Priority Data

Oct. 17, 2019 (KR) ........................ 10-2019-0129250

(51) Int. Cl.
*C12M 1/04* (2006.01)
*C12M 1/00* (2006.01)
*C12M 1/12* (2006.01)

(52) U.S. Cl.
CPC ............ *C12M 23/24* (2013.01); *C12M 23/20* (2013.01); *C12M 25/02* (2013.01); *C12M 25/06* (2013.01); *C12M 29/20* (2013.01)

(58) Field of Classification Search
CPC ...... C12M 23/24; C12M 23/20; C12M 25/02; C12M 25/06; C12M 29/20
See application file for complete search history.

(56) References Cited

U.S. PATENT DOCUMENTS 4,661,455 A * 4/1987 Hubbard ................ C12M 29/04 435/297.5
5,523,236 A 6/1996 Nuzzo
(Continued)

FOREIGN PATENT DOCUMENTS

CN 104379723 A 2/2015
CN 106676005 A 5/2017
(Continued)

OTHER PUBLICATIONS

JP-2017085960 Translation (Year: 2017).*
(Continued)

*Primary Examiner* — William H. Beisner
*Assistant Examiner* — Danielle B Henkel
(74) *Attorney, Agent, or Firm* — BROADVIEW IP LAW, PC

(57) ABSTRACT

A cell culture device is provided. A cell culture device according to an exemplary embodiment of the present invention comprises: a housing which has a plurality of through-holes formed through at least one surface thereof to allow carbon dioxide to be introduced thereinto from the outside and includes an inner space filled with a medium for culturing cells; a plurality of supporters which are arranged in the inner space in multiple steps while being spaced at an interval from each other so as to culture cells and are
(Continued)

provided in a plate-shape having a predetermined area; and a porous member which is attached to one surface of the housing so as to cover the plurality of through-holes, prevents the medium filled in the inner space from leaking to the outside, and allows carbon dioxide to be introduced into the inner space from the outside.

14 Claims, 11 Drawing Sheets

(56) References Cited

U.S. PATENT DOCUMENTS 5,605,835 A * 2/1997 Hu ........................ C12M 25/12 435/297.2
2004/0029265 A1* 2/2004 Doi ........................ C12M 29/16 435/297.1
2005/0054086 A1* 3/2005 Ophardt ................ C12M 23/28 435/296.1
2005/0095695 A1 5/2005 Shindler et al.
2007/0026516 A1 2/2007 Martin et al.
2010/0304472 A1* 12/2010 Kim ...................... C12M 23/44 435/304.1
2015/0056703 A1* 2/2015 Johnson .............. C12N 5/0667 435/289.1
2016/0083685 A1* 3/2016 Niazi .................... C12M 25/16 435/308.1
2016/0137961 A2* 5/2016 Clark .................... C12M 21/08 435/304.2
2018/0057784 A1* 3/2018 Wang .................... C12M 27/02
2018/0201891 A1* 7/2018 Ubukata ................ C12M 23/22
2019/0010437 A1 1/2019 Yuan et al.

FOREIGN PATENT DOCUMENTS

CN 109563459 A 4/2019
JP 2007-510820 A 4/2007
JP 2009-502165 A 1/2009
JP 2011-528226 A 11/2011
JP 2017-85960 A 5/2017
JP 2017085960 A * 5/2017
JP 2018-23291 A 2/2018
KR 10-2008-0072022 A 8/2008
KR 10-1393108 B1 5/2014
KR 10-2015-0111535 A 10/2015
KR 10-2017-0008024 A 1/2017
WO 2010/008566 A2 1/2010

OTHER PUBLICATIONS

International Search Report by Korean Intellectual Property Office for PCT/KR2020/013852 dated Jan. 27, 2021.
Office Action for CN 2020800730188 by China National Intellectual Property Administration dated Jan. 24, 2025.

* cited by examiner

10

170

114

20

CULTURE MEDIUM SUPPLY PART 100,200

115

CELL CULTURE DEVICE

CROSS-REFERENCE TO RELATED APPLICATIONS

This application is a National Phase Entry Application of PCT Application No. PCT/KR2020/013852 filed on Oct. 12, 2020, which claims priority to Korean Patent Application No. 10-2019-0129250 filed on Oct. 17, 2019 in Korean Intellectual Property Office, the entire contents of which is hereby incorporated by reference in its entirety.

TECHNICAL FIELD

The present invention relates to a cell culture device, and more particularly, to a stationary culture medium-type cell culture device that may be used in a cell culture system in which a culture medium is not circulated during cell culture.

BACKGROUND ART

Cell culture is a method of culturing and proliferating cells in a tissue slice, which is removed from an individual of a multicellular organism, in a vessel by nourishing the tissue slice.

In the field of biotechnology which has been rapidly developing since the 1980s, animal cell culture technology has played an important role, and the importance of animal cell mass culture technology began to emerge since the mid-1980s.

Animal cells derived from human or animal tissues may be cultured by suspension in a culture medium or adhesion to a carrier. Mostly, blood cell-derived cells (including hematopoietic stem cells) are suspension cells, and cells derived from tissues such as skin, liver, or lungs and embryonic stem cells or mesenchymal stem cells, etc. are adherent cells. Suspension cells can proliferate alone in a state in which the cells are suspended in a culture medium, but adherent cells can proliferate only when adhered to a surface of a support body.

Accordingly, since suspension cells are advantageous for maintaining the highest cell density per unit volume during scale-up, the development of mass culture methods has mainly been made for suspension cells, and the development of methods or systems for mass culture of adherent cells is insufficient.

DISCLOSURE

Technical Problem

The present invention is directed to providing a cell culture device that may be used in a cell culture system in which a large number of adherent cells are cultured through a single process.

The present invention is also directed to providing a cell culture device capable of, while enabling mass cell culture through a single process, reducing the consumption of culture medium and facilitating culture of sensitive cells.

Technical Solution

The present invention provides a cell culture device including: a housing in which a plurality of through-holes are formed in at least one surface to allow carbon dioxide to enter from the outside and which has an inner space filled with a culture medium for cell culture; a plurality of support bodies which are disposed in multiple stages at predetermined intervals from each other in the inner space for cell culture and which are provided in the shape of a plate having a predetermined area; and a porous member which is attached to one surface of the housing to cover the plurality of through-holes and is configured to prevent external leakage of the culture medium filled in the inner space and allow carbon dioxide to enter the inner space from the outside.

In one embodiment, the support body may include a motif-coated, plate-shaped nanofiber membrane. Here, the support body may include the motif-coated, plate-shaped nanofiber membrane and a support member which is attached to one surface of the nanofiber membrane via an adhesive layer to support the nanofiber membrane.

Also, the support body may include a plurality of holes formed to pass through the support member to facilitate passage of carbon dioxide entering the inner space through the plurality of through-holes. In such a case, a first area which is a sum of areas of the plurality of holes may be relatively smaller than a second area which is an area excluding the first area from the entire area of the support member.

As another example, the support body may be a plasma-treated, plate-shaped film member. In such a case, the plasma-treated, plate-shaped film member may include a plurality of holes formed to pass therethrough to facilitate passage of carbon dioxide entering the inner space through the plurality of through-holes, and a first area which is a sum of areas of the plurality of holes may be relatively smaller than a second area which is an area excluding the first area from the entire area of the plasma-treated, plate-shaped film member.

Also, the plurality of support bodies may maintain a state in which two support bodies adjacent to each other are spaced apart via a spacer disposed in the inner space.

For example, the spacer may include two guide members inserted into the inner space so that one surface of one guide member and one surface of the other guide member face each other, and the two guide members may include a plurality of slot grooves formed to be recessed in a longitudinal direction so that end sides of the support bodies are able to be fitted to the surfaces facing each other. Here, the two guide members may be disposed so that one surface of each guide member comes into contact with one of two inner surfaces that face each other among inner surfaces of the housing.

Also, the porous member may be a membrane treated to be water-repellent.

Also, the housing may include at least one culture medium inlet disposed at a side portion of the housing to allow a culture medium supplied from the outside to enter the inner space.

Meanwhile, the cell culture device may further include a blower fan coupled to the housing to suction carbon dioxide present outside the housing and supply the suctioned carbon dioxide into the plurality of through-holes.

In such a case, the housing may include a concave portion formed to be recessed a predetermined depth inward in one surface, the plurality of through-holes may be formed to pass through a bottom surface of the concave portion, and a lid member on which the blower fan is mounted may be coupled to the housing to cover an open upper portion of the concave portion. Here, the blower fan may be disposed to be spaced a predetermined distance apart from the plurality of through-holes.

Also, carbon dioxide present outside the housing may enter the concave portion through the blower fan and then be dispersed and injected into the inner space through the plurality of through-holes.

Advantageous Effects

According to the present invention, since mass cell culture is possible through a single process and the consumption of culture medium can be reduced, cost reduction can be achieved, and since an occurrence of stress during cell culture can be minimized, culture of sensitive cells vulnerable to stress can be facilitated.

MODES OF THE INVENTION

Figure 1:
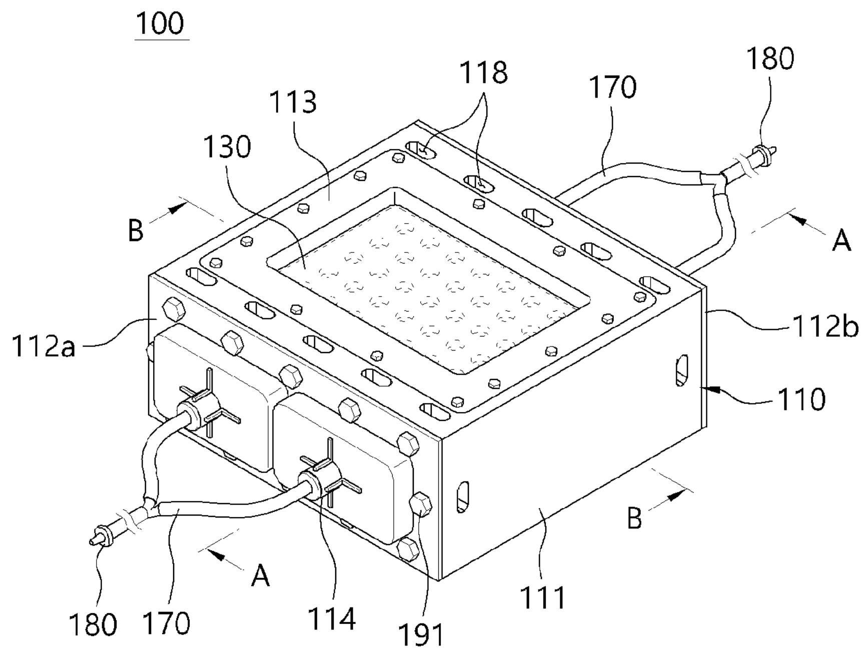
FIG. 1 is a schematic diagram illustrating a cell culture device according to one embodiment of the present invention.

Hereinafter, embodiments of the present invention will be described in detail with reference to the accompanying drawings to allow those of ordinary skill in the art to which the present invention pertains to easily carry out the present invention. The present invention may be implemented in various different forms and is not limited to the embodiments described herein. In the drawings, parts unrelated to the description have been omitted for clear description of the present invention, and like reference numerals are assigned to like or similar components throughout.

Cell culture devices 100 and 200 according to one embodiment of the present invention may be filled with a culture medium supplied from the outside in a state in which a plurality of support bodies 120 and 220 to which cells to be cultured are adhered are mounted therein. Also, as carbon dioxide of a predetermined concentration continuously enters the cell culture devices 100 and 200, the culture medium may be constantly maintained at a pH level suitable for cell culture.

In this way, in the cell culture devices 100 and 200 according to one embodiment of the present invention, culture of the cells adhered to each of the support bodies 120 and 220 may be facilitated by nutrients supplied from the culture medium.

Figure 9:
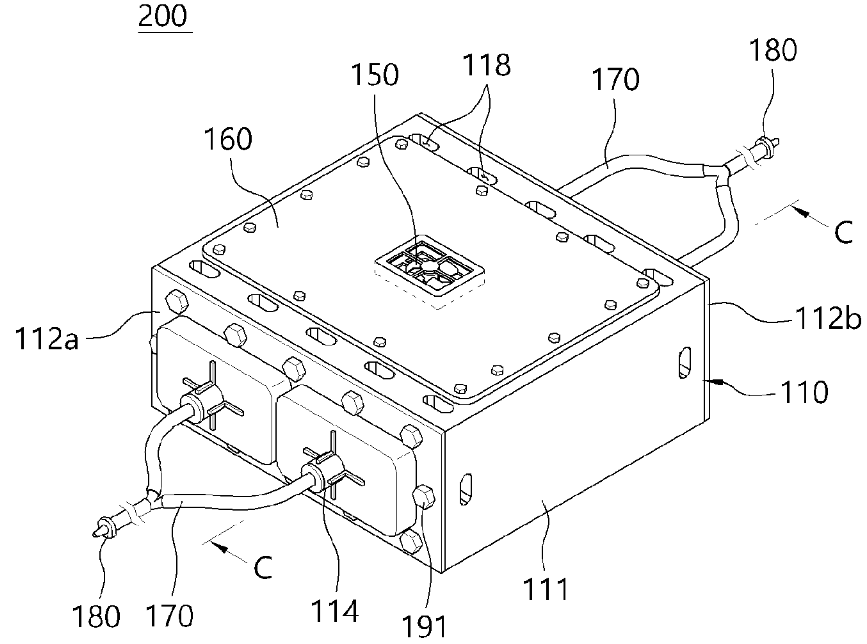
FIG. 9 is a schematic diagram illustrating a cell culture device according to another embodiment of the present invention.
Figure 10:
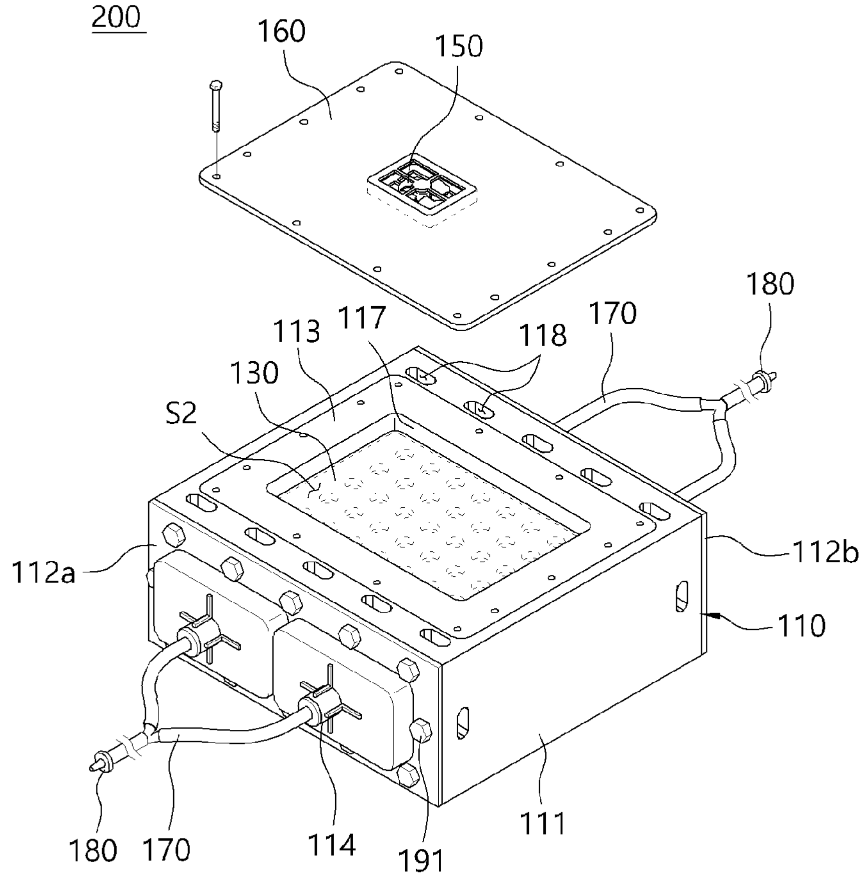
FIG. 10 is a view illustrating a state in which a lid member is separated from a housing in FIG. 9.

To this end, as illustrated in FIGS. 1 and 9, the cell culture devices 100 and 200 according to one embodiment of the present invention include a housing 110, the plurality of support bodies 120 and 220, and a porous member 130.

The housing 110 may accommodate the plurality of support bodies 120 and 220 and the culture medium. To this end, the housing 110 may be formed in the shape of a vessel having an inner space S1.

Figure 2:
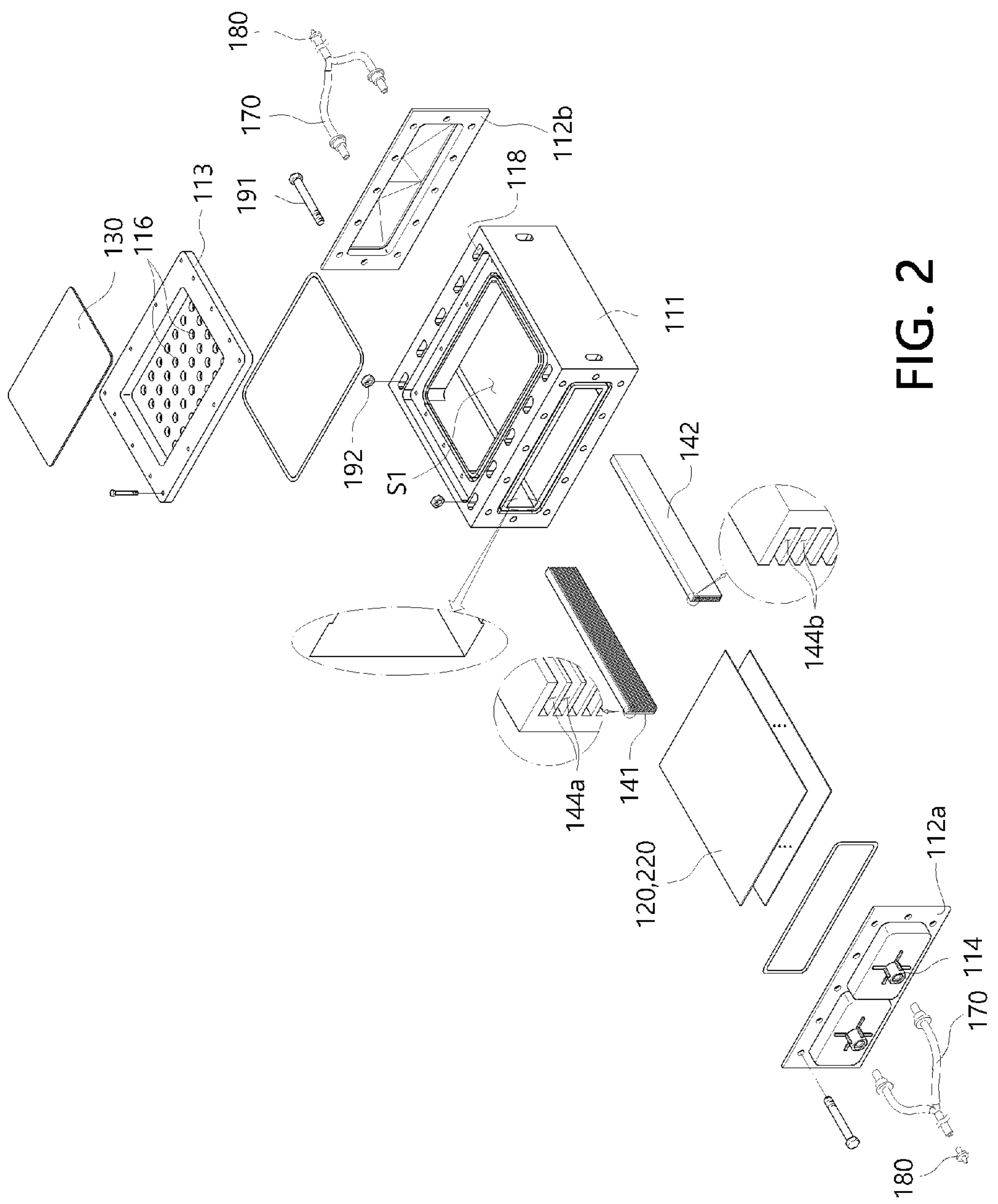
FIG. 2 is an exploded view of FIG. 1.
Figure 11:
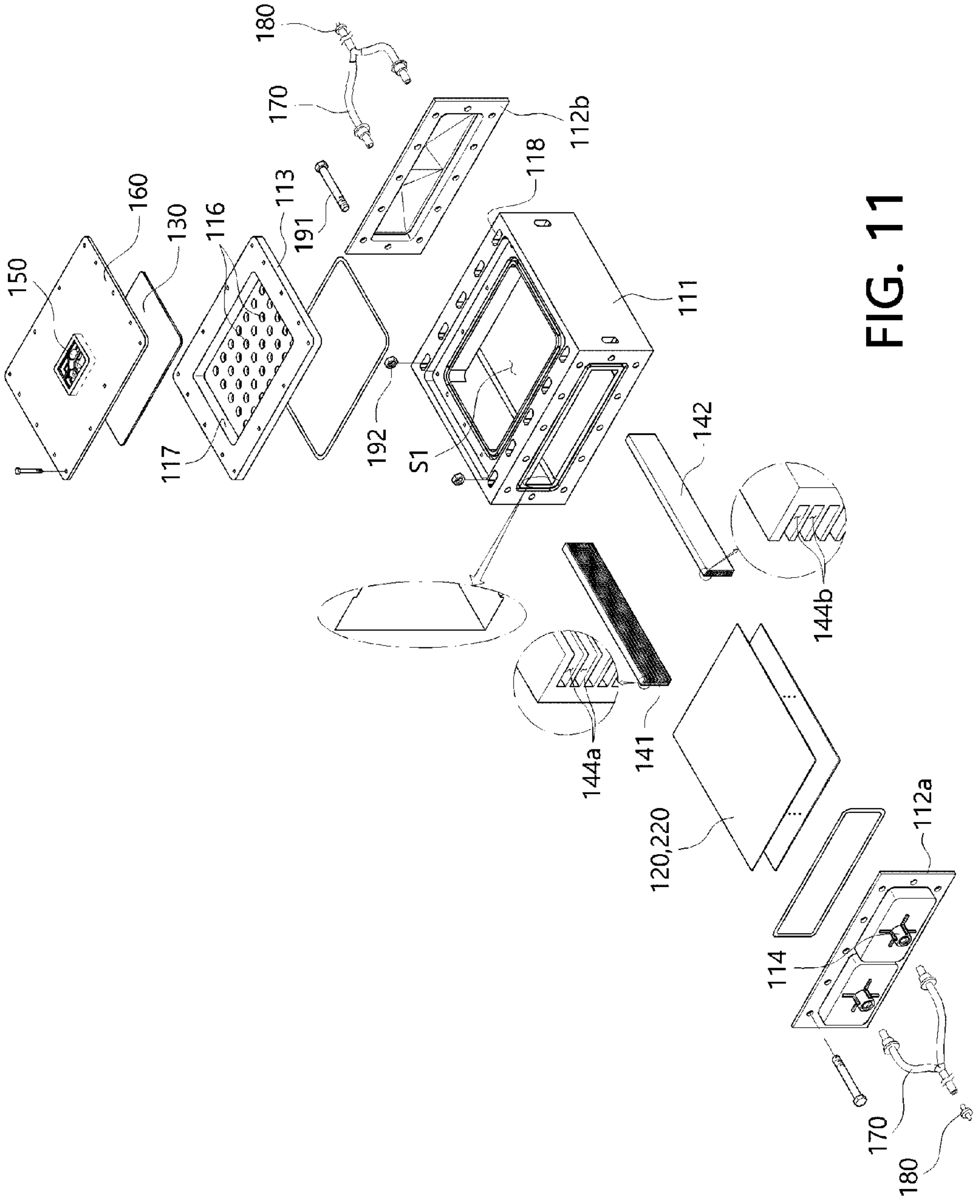
FIG. 11 is an exploded view of FIG. 9.

For example, as illustrated in FIGS. 2 and 11, the housing 110 may include a vessel-shaped body 111 having the inner space S1 whose front surface, rear surface, and upper surface are open.

In such a case, a cap part 112*a* in which at least one culture medium inlet 114 is formed and a second cap part 112*b* in which at least one culture medium outlet 115 is formed may be respectively coupled to the front surface and rear surface of the body 111, and the open upper portion of the inner space S1 may be closed by a cover member 113 fastened to the body 111. In this way, the culture medium supplied from the outside may fill the inner space S1 through the culture medium inlet 114, the culture medium filled in the inner space S1 may supply nutrients necessary for cell culture to the cells, and after cell culture is completed, the culture medium filled in the inner space S1 may be discharged to the outside through the culture medium outlet 115.

Here, a separate tube 170 may be connected to the culture medium inlet 114 and the culture medium outlet 115, and an anti-contamination stopper 180 that can prevent leakage of the culture medium while preventing entry of bacteria may be detachably coupled to an end portion of the tube 170. Also, in a case in which the front surface and rear surface of the body 111 are closed, the culture medium inlet 114 and the culture medium outlet 115 may be directly formed in the front surface and rear surface, respectively, of the body 111. Further, the cover member 113 may be integrally formed with the body 111.

Figure 3:
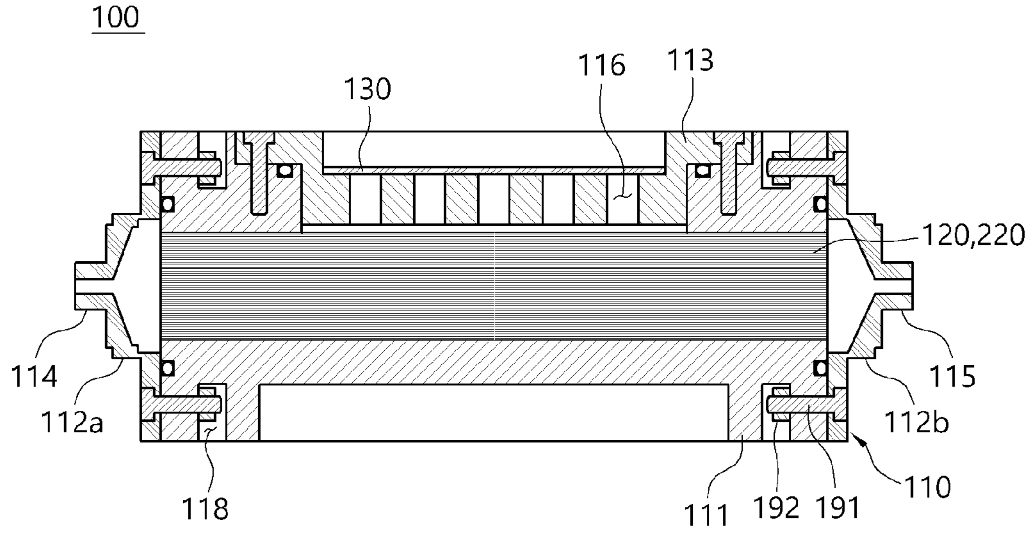
FIG. 3 is a cross-sectional view taken along line A-A of FIG. 1.
Figure 4:
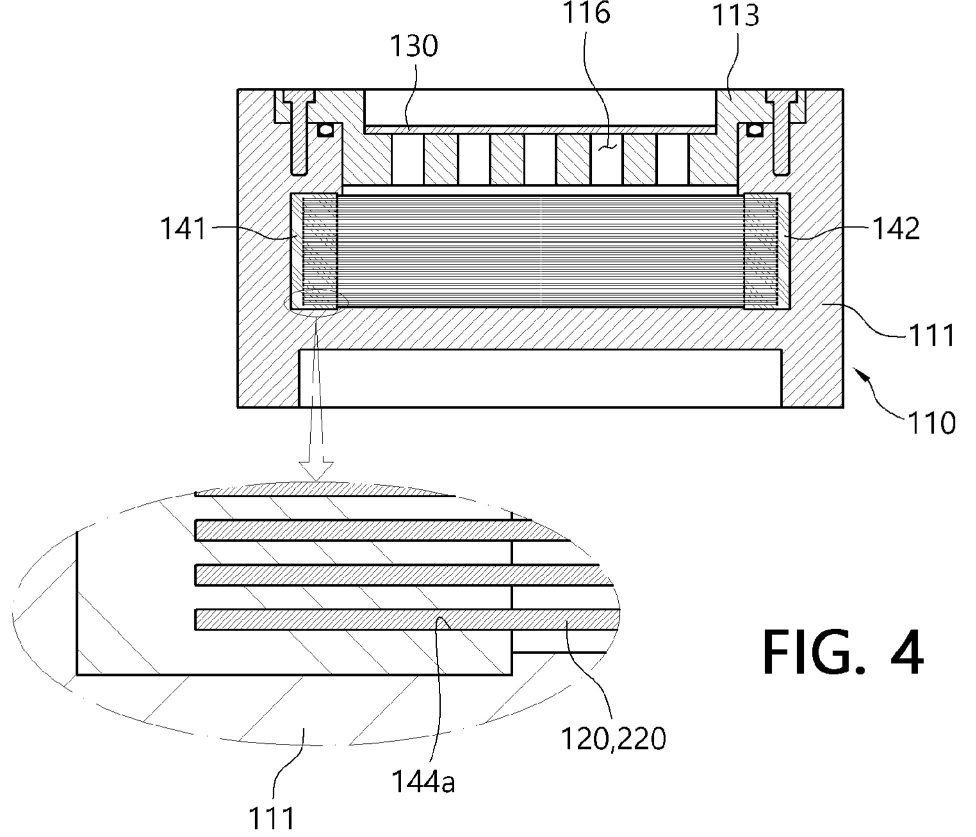
FIG. 4 is a cross-sectional view taken along line B-B of FIG. 1.
Figures 12, 13:
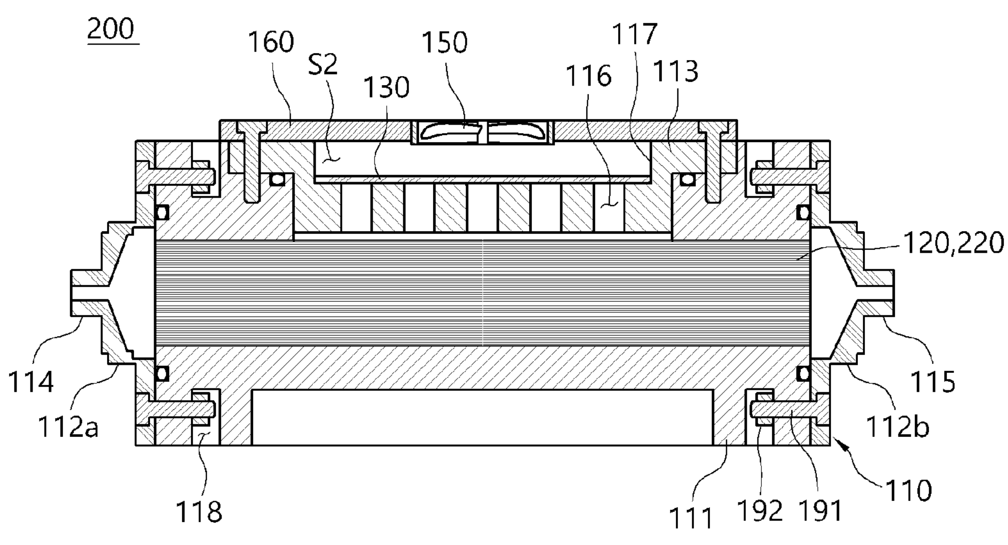
FIG. 12 is a cross-sectional view taken along line C-C of FIG. 9.
FIG. 13 is a view schematically illustrating a state in which the cell culture device according to one embodiment of the present invention is applied to a cell culture system.

Also, an accommodation hole 118 recessed inward may be formed in one side of the body 111. In a case in which the first cap part 112*a* and the second cap part 112*b* are fastened to the body 111 through a bolt member 191 as illustrated in FIGS. 3 and 12, an end portion of the bolt member 191 may protrude toward the accommodation hole 118, and a nut member 192 for fixing the bolt member 191 may be accommodated in the accommodation hole 118. Accordingly, by fastening the bolt member 191 and the nut member 192 using the accommodation hole 118, a worker may couple the first cap part 112*a* and the second cap part 112*b* to the body 111.

Meanwhile, the cell culture devices 100 and 200 according to one embodiment of the present invention may include a plurality of through-holes 116 formed to communicate with the inner space S1 to facilitate entry of carbon dioxide into the inner space S1.

For example, the plurality of through-holes 116 may be formed to pass through the cover member 113.

Accordingly, during cell culture using the cell culture devices 100 and 200 according to one embodiment of the present invention as illustrated in FIG. 13, when the cell culture devices 100 and 200 are placed inside a chamber such as an incubator 10, carbon dioxide present inside the incubator 10 may be supplied into the inner space S1 of the housing 110, in which the plurality of support bodies 120 and 220 are disposed, through the plurality of through-holes 116.

Here, the incubator 10 may be a space that provides a culture environment for the cells adhered to the plurality of support bodies 120 and 220.

For example, the incubator 10 may be a chamber as illustrated in FIG. 13, the inside of the chamber may be an environment in which temperature and carbon dioxide concentration are maintained to be constant, and a culture medium supply part 20 for supplying a culture medium to the cell culture devices 100 and 200 may be disposed inside the chamber.

In such a case, the incubator 10 may include an air conditioning system for maintaining the temperature inside the incubator 10 at a predetermined temperature and include a carbon dioxide supply means (not illustrated) or the like for stably supplying carbon dioxide into the incubator 10 to maintain carbon dioxide concentration inside the incubator 10 at a predetermined level. Further, the cell culture devices 100 and 200 may be selectively connected to the culture medium supply part 20 in a case in which supply or replacement of culture medium is necessary.

In this way, in the cell culture devices 100 and 200 disposed inside the incubator 10, carbon dioxide present inside the incubator 10 may be supplied into the inner space S1 of the housing 110 through the plurality of through-holes 116, and carbon dioxide supplied into the inner space S1 may be dissolved in the culture medium filled in the inner space S1, and thus the culture medium may be always maintained at a suitable pH level necessary for cell culture.

Thus, in the cell culture devices 100 and 200 according to one embodiment of the present invention, even when cell culture occurs in a state in which the culture medium disposed inside the incubator 10 and filled in the inner space S1 does not circulate, carbon dioxide present inside the incubator 10 may be continuously supplied to the culture medium filled in the inner space S1 through the plurality of through-holes 116.

Thus, since the culture medium filled in the inner space S1 is maintained at a suitable pH level required for cell culture, culture of the cells adhered to each of the support bodies 120 and 220 may be facilitated.

Accordingly, the cell culture devices 100 and 200 according to one embodiment of the present invention can achieve cost reduction by minimizing the use amount of culture medium necessary for cell culture. Also, since the culture medium necessary for cell culture is always maintained in a state of being stationary in the inner space S1 of the housing 110 and thus an occurrence of stress that may be applied to the cells adhered to each of the support bodies 120 and 220 can be minimized, culture of sensitive cells vulnerable to stress can be facilitated.

Cells to be cultured may be adhered to the plurality of support bodies 120 and 220. The support bodies 120 and 220 may be provided in the shape of a plate having a predetermined area to culture a large number of cells through one culture.

Further, in the cell culture devices 100 and 200 according to one embodiment of the present invention, the plurality of support bodies 120 and 220, which are formed in the plate shape and to which the cells to be cultured are adhered, may be disposed in multiple stages in the inner space S1 of the housing 110.

Thus, in the cell culture devices 100 and 200 according to one embodiment of the present invention, by increasing a degree of integration of the support bodies 120 and 220 where cell culture occurs, a larger number of cells may be cultured through one culture.

Further, in the cell culture devices 100 and 200 according to one embodiment of the present invention, since the plurality of support bodies 120 and 220 are disposed in a form of being stacked in multiple stages inside a single device, the size of the overall equipment can be reduced while allowing mass cell culture.

Here, various known materials used in cell culture may be used as a material of the support bodies 120 and 220 without limitations as long as the support bodies 120 and 220 can be implemented in the plate shape and cells can be easily adhered to the support bodies 120 and 220.

Figure 6:
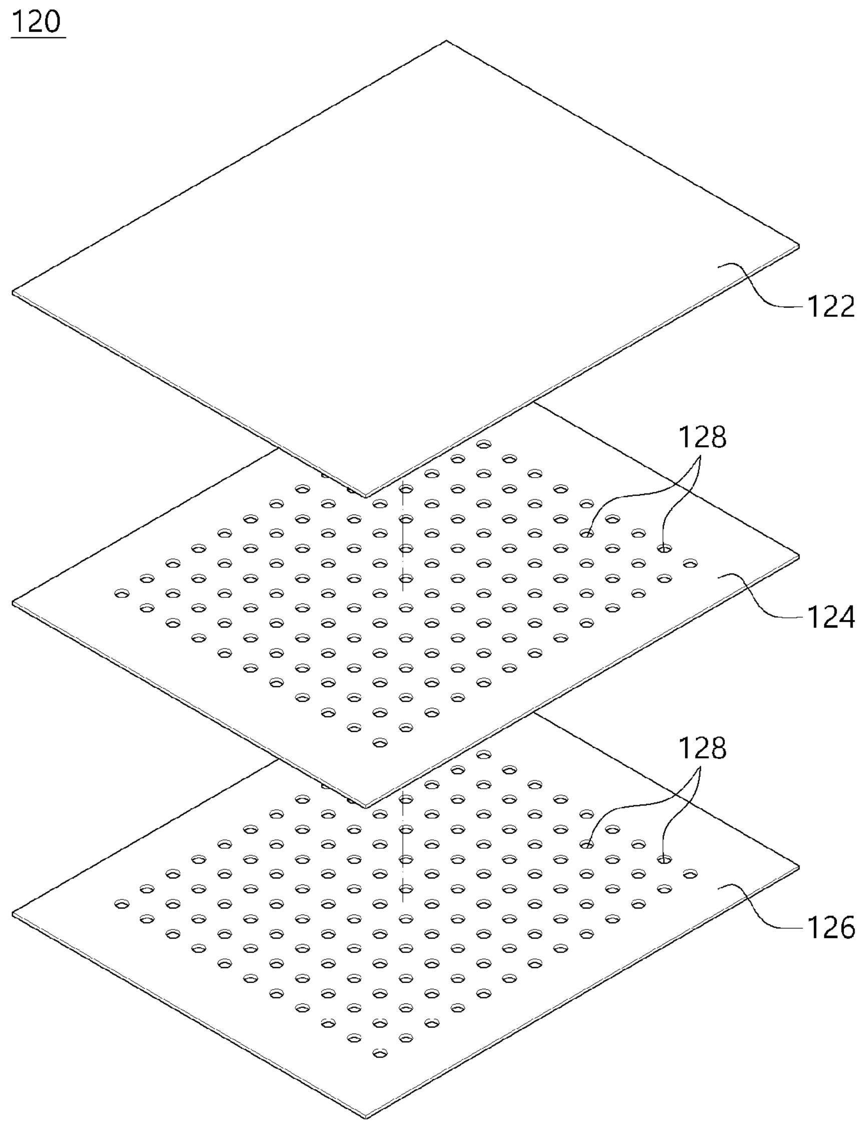
FIG. 6 is a view illustrating one form of support body that may be used in the cell culture device according to one embodiment of the present invention.

For example, the support body 120 may include a nanofiber membrane 122 in which nanofibers are formed in a three-dimensional network structure by electrospinning. In such a case, as illustrated in FIG. 6, the support body 120 may have a three-layer structure which includes the nanofiber membrane 122 and further includes a support member 126 attached to one surface of the nanofiber membrane 122 via an adhesive layer 124. Here, the support member 126 may be a plate-shaped film member and may support the one surface of the nanofiber membrane 122. In this way, even when the nanofiber membrane 122 is formed in the shape of a plate with flexibility, the nanofiber membrane 122 may be supported by the support member 126, and thus bending or sagging of the nanofiber membrane 122 may be prevented. Accordingly, since the support bodies 120 and 220 are maintained in a state of being unfolded in the inner space S1 of the housing 110, cell culture may be facilitated.

Figure 7:
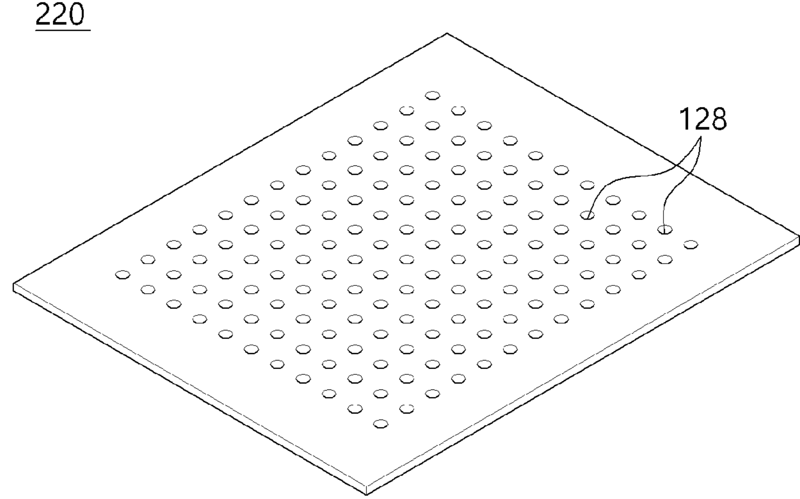
FIG. 7 is a view illustrating another form of support body that may be used in the cell culture device according to one embodiment of the present invention.

As another example, as illustrated in FIG. 7, the support body 220 may be a plate-shaped film member having a predetermined area.

In such a case, surfaces of the support bodies 120 and 220 may be modified to facilitate adhesion of cells to be cultured. For example, in a case in which the support body 120 includes the nanofiber membrane 122, the nanofiber membrane 122 may be a membrane in which motif is applied to a surface of nanofibers. Also, in a case in which the support body 220 is provided as a plate-shaped film member, the film member may be a plasma-treated film member.

The porous member 130 may be formed as a plate-shaped member having a predetermined area and may be attached to the cover member 113 to cover the plurality of through-holes 116 formed in the cover member 113.

The porous member 130 may, while blocking passage of foreign matter and liquids, allow passage of gases such as carbon dioxide. In this way, supply of carbon dioxide, which enters through the porous member 130 and the plurality of through-holes 116, to the culture medium filled in the inner space S1 may be facilitated while other foreign matter does not enter.

Accordingly, an occurrence of contamination of the culture medium filled in the inner space S1 due to other foreign matter may be prevented.

For example, the porous member 130 may be a nanofiber membrane treated to be water-repellent. However, the material of the porous member 130 is not limited thereto, and any material that allows passage of a gaseous fluid while blocking passage of solid and liquid fluids may be used without limitations.

Meanwhile, the cell culture devices 100 and 200 according to one embodiment of the present invention may include a plurality of holes 128 formed in the support bodies 120 and 220 to facilitate supply of carbon dioxide regardless of the position of the culture medium filled in the inner space S1 even when the number of support bodies 120 and 220 stacked and arranged in multiple layers in the inner space S1 is increased.

The plurality of holes 128 may allow carbon dioxide, which is supplied into the inner space S1 through the plurality of through-holes 116, to pass through the support bodies 120 and 220 and move downward, thus improving flowability of carbon dioxide.

To this end, the plurality of holes 128 may be formed in a portion of the support bodies 120 and 220 that does not allow passage of gases.

For example, in the case in which the support body 120 is provided to have the three-layer structure including the motif-coated nanofiber membrane 122, the adhesive layer 124, and the support member 126, the plurality of holes 128 may be formed in the support body 120 to pass through both the adhesive layer 124 and the support member 126.

Also, in the case in which the support body 220 is provided as a plasma-treated, plate-shaped film member, the plurality of holes 128 may be formed to pass through the film member.

Accordingly, carbon dioxide entering the inner space S1 of the housing 110 through the plurality of through-holes 116 may easily move downward through the plurality of holes 128 formed in the support bodies 120 and 220.

Thus, regardless of the position of the culture medium filled in the inner space S1, carbon dioxide may be supplied to the culture medium through the plurality of through-holes 116.

Here, a first area which is a sum of areas of the plurality of holes 128 formed in the support bodies 120 and 220 may be relatively smaller than a second area which is a remaining area excluding the first area from the support bodies 120 and 220.

For example, in the entire area of the support member 126, a first area which is a sum of areas where the plurality of holes 128 are formed may be an area that is relatively smaller than a second area which corresponds to the remaining areas where the holes are not formed, and in the entire area of the support body 220 provided as a plasma-treated film member, a first area which is a sum of areas where the plurality of holes 128 are formed may be an area that is relatively smaller than a second area which corresponds to the remaining areas where the holes are not formed.

This is to secure a support force for maintaining the plate shape while securing flowability of carbon dioxide passing through the plurality of holes 128.

Figure 8A:
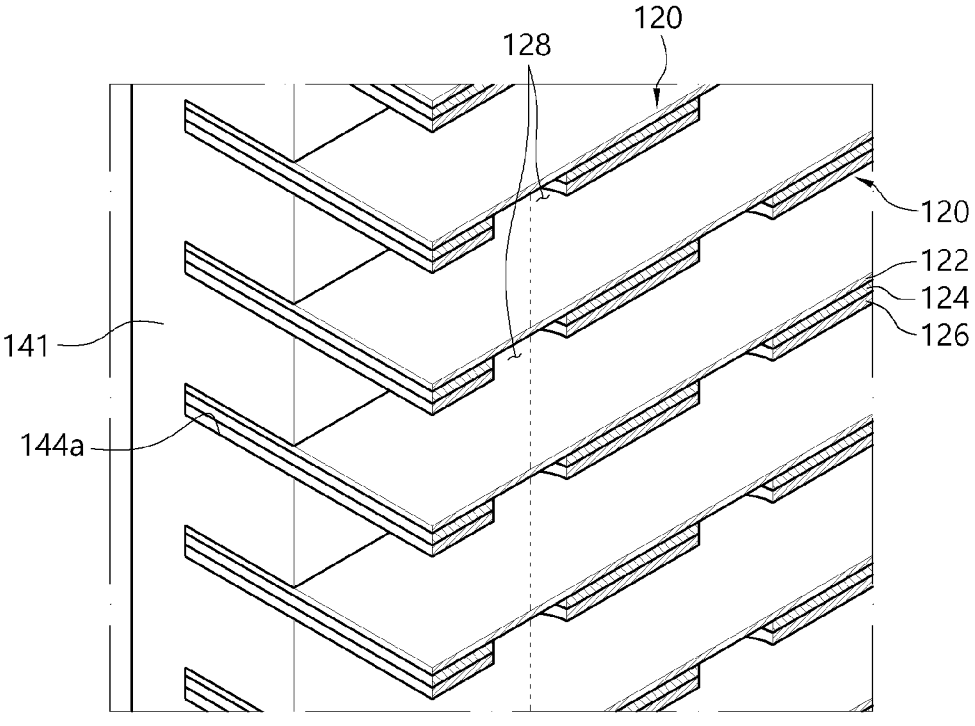
FIGS. 8A and 8B are views conceptually illustrating manners of arrangement of holes formed in each support body when the support body of FIG. 7 is arranged in one direction.
Figure 8B:
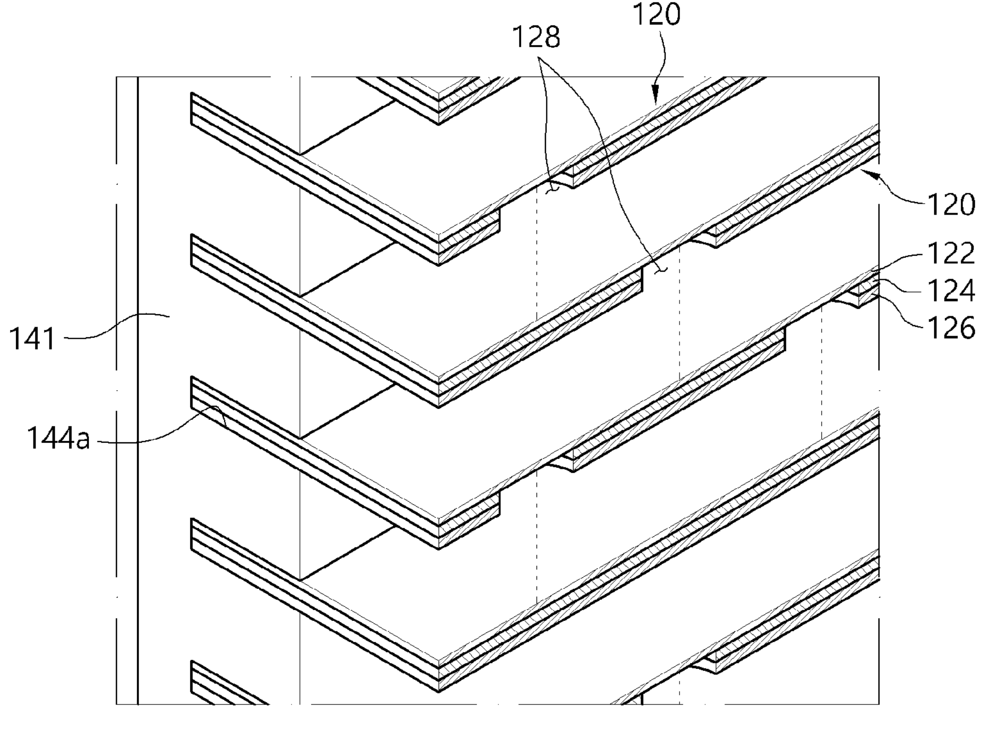

Here, in the case in which the plurality of support bodies 120 and 220 each including the plurality of holes 128 are disposed in multiple stages in the inner space S1, the plurality of support bodies 120 may be disposed so that the plurality of holes 128 formed in each support body 120 are collinear in a stacking direction as illustrated in FIG. 8A or may be disposed so that the plurality of holes 128 formed in each support body 120 are alternately placed as illustrated in FIG. 8B.

Further, although the support body 120 having the form illustrated in FIG. 6 is illustrated as an example in FIGS. 8A and 8B, the present invention is not limited thereto, and the manners in which the holes 28 are disposed that are illustrated in FIGS. 8A and 8B may identically apply to the support body 220 having the form illustrated in FIG. 7.

Meanwhile, the cell culture device 200 according to one embodiment of the present invention may further include a blower fan 150 to facilitate supply of carbon dioxide from the outside into the inner space S1 even in a state in which the culture medium filled in the inner space S1 is stationary instead of circulating.

The blower fan 150 may suction carbon dioxide present outside the housing 110 and supply the suctioned carbon dioxide into the plurality of through-holes 116 and thus may facilitate supply of carbon dioxide into the inner space S1 of the housing 110 through the plurality of through-holes 116.

To this end, the cell culture device 200 according to one embodiment of the present invention may further include the blower fan 150 coupled to the housing 110 as illustrated in FIGS. 9 to 12, and the blower fan 150 may be disposed to be placed above the plurality of through-holes 116 formed in the cover member 113.

For example, the housing 110 may include a concave portion 117 formed to be recessed a predetermined depth inward in one surface, and the plurality of through-holes 116 may be formed to pass through a bottom surface of the concave portion 117. Here, the one surface of the housing 110 in which the concave portion 117 is formed may be the cover member 113 described above, and the porous member 130 described above may be attached to the bottom surface of the concave portion 117 to cover the plurality of through-holes 116.

In such a case, a lid member 160 on which the blower fan 150 is mounted may be coupled to the housing 110 to cover an open upper portion of the concave portion 117, and the blower fan 150 mounted on the lid member 160 may be spaced a predetermined distance apart from the bottom surface of the concave portion 117.

In this way, a residence space S2 of a predetermined volume that is defined by the concave portion 117 and the lid member 160 may be formed at one surface of the housing 110, carbon dioxide present outside the housing 110 may be suctioned into the residence space S2 by operation of the blower fan 150, and carbon dioxide suctioned into the residence space S2 may easily move into the inner space S1 of the housing through the plurality of through-holes 116 formed in the bottom surface of the concave portion 117.

Thus, in the cell culture device 200 according to one embodiment of the present invention, even when the plurality of support bodies 120 and 220 are disposed with a high degree of integration in the inner space S1 of the housing 110, carbon dioxide may be forcibly supplied into the inner space S1 by the blower fan 150, and thus supply of carbon dioxide to the culture medium filled in the inner space S1 may be facilitated regardless of the position of the culture medium.

Accordingly, in the cell culture device 200 according to one embodiment of the present invention, even when the plurality of support bodies 120 and 220 are disposed with a high degree of integration, culture of cells adhered to each of the support bodies 120 and 220 may be facilitated, and thus a large number of cells can be cultured through one culture process.

Meanwhile, the cell culture devices 100 and 200 according to one embodiment of the present invention may include a spacer which is for, while increasing the degree of integration of the plurality of support bodies 120 and 220 disposed in multiple stages in the inner space S1, maintaining a state in which the support bodies 120 and 220 are spaced apart at predetermined intervals from each other.

For example, as illustrated in FIGS. 2 to 4 and FIGS. 11 and 12, the spacer may include two guide members 141 and 142 inserted into the inner space S1 so that one surface of one guide member and one surface of the other guide member face each other, and the two guide members 141 and 142 may be a first guide member 141 and a second guide member 142 which are disposed at the left side in FIG. 2.

In such a case, a plurality of slot grooves 144*a* and 144*b* formed to be recessed in a height direction may be formed in opposing surfaces of the first guide member 141 and the second guide member 142 that face each other, and the first guide member 141 and the second guide member 142 may be disposed so that surfaces in which the slot grooves 144*a* and 144*b* are not formed, which are opposite to the surfaces in which the slot grooves 144*a* and 144*b* are formed, come into contact with two inner surfaces that face each other among inner surfaces of the housing 110.

In this way, the first guide member 141 and the second guide member 142 may be disposed in the inner space S1 so that the surfaces on which the slot grooves 144*a* and 144*b* are formed face each other.

Accordingly, when the support bodies 120 and 220 are inserted into the slot grooves 144*a* and 144*b* in a state in which the first guide member 141 and the second guide member 142 are inserted into the inner space S1, each of both side ends of the support bodies 120 and 220 may be inserted into one of the slot grooves 144*a* formed in the first guide member 141 and the slot grooves 144*b* formed in the second guide member 142.

Thus, due to both side ends of the support bodies 120 and 220 being constrained by the slot grooves 144*a* and 144*b*, the support bodies 120 and 220 may be disposed in a horizontal state in the inner space S1, and two support bodies 120 and 220 that are adjacent to each other may remain spaced apart by as much as an interval between two slot grooves formed in the height direction.

In this way, both surfaces of the plurality of support bodies 120 and 220 disposed in multiple stages in the inner space S1 may easily come into contact with the culture medium filled in the inner space S1, and culture of the cells adhered to the support bodies 120 and 220 may be facilitated by nutrients supplied from the culture medium.

In this way, since the plurality of support bodies 120 and 220 may be mounted by sliding in the cell culture devices 100 and 200 according to one embodiment of the present invention, convenience of assembly can be improved.

Meanwhile, in the cell culture devices 100 and 200 according to one embodiment of the present invention, the spacer may consist of three or more guide members 141, 142, and 143 to further improve the degree of integration of the support bodies 120 and 220 disposed in the inner space S1 of the housing 110.

Figure 5:
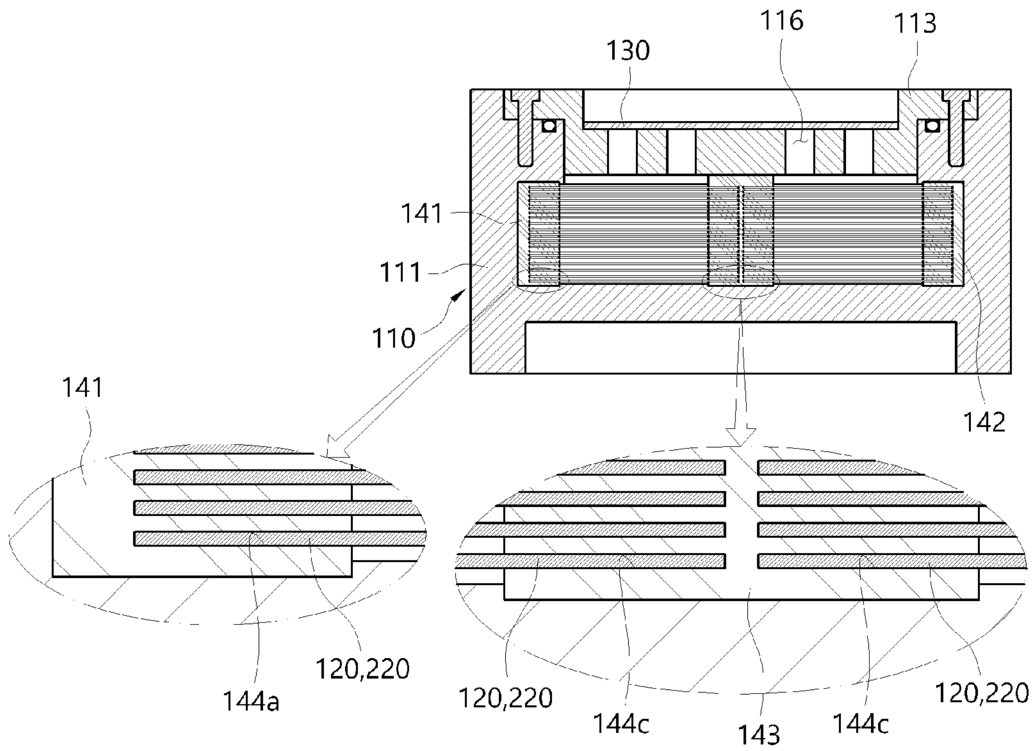
FIG. 5 is a cross-sectional view taken along line B-B of FIG. 1 and illustrates a case in which a plurality of support bodies are arranged in a plurality of rows in an inner space of a housing in the cell culture device according to one embodiment of the present invention.

For example, as illustrated in FIG. 5, the spacer may include the first guide member 141 and the second guide member 142, which are inserted into the inner space S1 so that one surface of one guide member and one surface of the other guide member face each other, and a third guide member 143 disposed at a central portion of the inner space S1.

In such a case, both surfaces of the third guide member 143 may respectively face one surface of the first guide member 141 and one surface of the second guide member 142, and a plurality of slot grooves 144*c* may be formed in each of both surfaces of the third guide member 143.

In this way, since the plurality of support bodies 120 and 220 may be mounted in multiple rows using the three guide members 141, 142, and 143, the degree of integration of the support bodies 120 and 220 may be further improved, and mass culture of a larger number of cells is possible. In such a case, the third guide member 143 may consist of two guide members that have slot grooves formed in only one surface.

However, the total number of guide members constituting the spacer is not limited thereto, and the spacer may consist of three or more guide members according to the total number of support bodies 120 and 220 to be mounted. The number of guide members may be set to any number without limitations as long as the guide members form a pair with each other.

Embodiments of the present invention have been described above, but the spirit of the present invention is not limited to the embodiments proposed herein. Those of ordinary skill in the art who understand the spirit of the present invention may easily propose other embodiments by addition, alteration, omission, etc. of components within the scope of the same spirit, but such embodiments also belong to the scope of the spirit of the present invention.

The invention claimed is:

1. A cell culture device comprising:

a housing in which a plurality of through-holes are formed in at least one surface to allow carbon dioxide to enter from the outside and which has an inner space filled with a culture medium for cell culture;

a plurality of support bodies which are disposed in multiple stages at predetermined intervals from each other in the inner space for cell culture, which are provided in the shape of a plate having a predetermined area; and a porous member which is attached to one surface of the housing to cover the plurality of through-holes and is configured to prevent external leakage of the culture medium filled in the inner space and allow carbon dioxide to enter the inner space from the outside, and wherein the plurality of support bodies maintain a state in which two support bodies adjacent to each other are spaced apart via a spacer disposed in the inner space, wherein the spacer includes a first guide member and a second guide member, which are inserted into the inner space so that one surface of the first guide member and one surface of the second guide member face each other, and a third guide member disposed at a central portion of the inner space, wherein the first guide member and the second guide member include a first plurality of slot grooves formed to be recessed in a longitudinal direction, wherein both surfaces of the third guide member respectively face one surface of the first guide member and one surface of the second guide member, and a second plurality of slot grooves is formed to be recessed in the longitudinal direction in each of both surfaces of the third guide member, wherein the plurality of support bodies are mounted in the multiple stages by being inserted into the first plurality of slot grooves and the second plurality of slot grooves.

2. The cell culture device of claim 1, wherein the support body includes a motif-coated, plate-shaped nanofiber membrane.

3. The cell culture device of claim 2, wherein the support body includes the motif-coated, plate-shaped nanofiber membrane and a support member which is attached to one surface of the nanofiber membrane via an adhesive layer to support the nanofiber membrane.

4. The cell culture device of claim 3, wherein the support body includes a plurality of holes formed to pass through the support member to facilitate passage of carbon dioxide entering the inner space through the plurality of through-holes.

5. The cell culture device of claim 4, wherein a first area which is a sum of areas of the plurality of holes is relatively smaller than a second area which is an area excluding the first area from the entire area of the support member.

6. The cell culture device of claim 1, wherein the support body is a plasma-treated, plate-shaped film member.

7. The cell culture device of claim 6, wherein the plasma-treated, plate-shaped film member includes a plurality of holes formed to pass therethrough to facilitate passage of carbon dioxide entering the inner space through the plurality of through-holes.

8. The cell culture device of claim 7, wherein a first area which is a sum of areas of the plurality of holes is relatively smaller than a second area which is an area excluding the first area from the entire area of the plasma-treated, plate-shaped film member.

9. The cell culture device of claim 1, wherein the two guide members are disposed so that one surface of each guide member comes into contact with one of two inner surfaces that face each other among inner surfaces of the housing.

10. The cell culture device of claim 1, wherein the porous member is a membrane treated to be water-repellent.

11. The cell culture device of claim 1, wherein the housing includes at least one culture medium inlet disposed at a side portion of the housing to allow a culture medium supplied from the outside to enter the inner space.

12. The cell culture device of claim 1, further comprising a blower fan coupled to the housing to suction carbon dioxide present outside the housing and supply the suctioned carbon dioxide into the plurality of through-holes.

13. The cell culture device of claim 12, wherein:

the housing includes a concave portion formed to be recessed a predetermined depth inward in one surface;

the plurality of through-holes are formed to pass through a bottom surface of the concave portion;

a lid member on which the blower fan is mounted is coupled to the housing to cover an open upper portion of the concave portion; and the blower fan is disposed to be spaced a predetermined distance apart from the plurality of through-holes.

14. The cell culture device of claim 13, wherein carbon dioxide present outside the housing enters the concave portion through the blower fan and then is dispersed and injected into the inner space through the plurality of through-holes.

* * * * *